(12) United States Patent
Horton et al.

(10) Patent No.: US 10,006,898 B2
(45) Date of Patent: Jun. 26, 2018

(54) ANALYTICAL METHOD FOR OPTIMIZING EFFICIENCY OF HYDROGEN SULFIDE SCAVENGERS

(71) Applicant: CANADIAN ENERGY SERVICES L.P., Calgary (CA)

(72) Inventors: David Horton, Calgary (CA); Jeffrey Soderberg, Calgary (CA); Wes Suhai, Calgary (CA)

(73) Assignee: Canadian Energy Services L.P., Calgary (CA)

( * ) Notice: Subject to any disclaimer, the term of this patent is extended or adjusted under 35 U.S.C. 154(b) by 0 days. days.

(21) Appl. No.: 15/336,449

(22) Filed: Oct. 27, 2016

(65) Prior Publication Data
US 2017/0269054 A1    Sep. 21, 2017

Related U.S. Application Data

(60) Provisional application No. 62/309,115, filed on Mar. 16, 2016.

(51) Int. Cl.
*C07C 7/11* (2006.01)
*G01N 33/28* (2006.01)
*C07C 7/00* (2006.01)

(52) U.S. Cl.
CPC .......... *G01N 33/287* (2013.01); *C07C 7/005* (2013.01); *C07C 7/11* (2013.01)

(58) Field of Classification Search
None
See application file for complete search history.

(56) References Cited

U.S. PATENT DOCUMENTS

| | | | | |
|---|---|---|---|---|
| 5,508,012 A | * | 4/1996 | Trauffer | C01B 17/22 423/206.1 |
| 8,404,031 B1 | * | 3/2013 | Callaway | B01D 53/02 502/406 |
| 8,759,252 B1 | * | 6/2014 | Callaway | B01J 20/041 502/406 |

* cited by examiner

*Primary Examiner* — Tam M Nguyen
(74) *Attorney, Agent, or Firm* — Borden Ladner Gervais LLP

(57) ABSTRACT

A method of determining sulfur content in an aqueous fluid containing spent hydrogen sulfide scavenger from a scrubber or contactor tower is described as is a method of optimizing the hydrogen sulfide scavenger treatment rate in a scrubber or contactor tower. The method includes the steps of providing a sample of an aqueous fluid from the scrubbing tower where the aqueous fluid contains spent hydrogen sulfide scavenger; and using x-ray fluorescence to determine the amount of total sulfur in the sample. The method may also use the total sulfur content in the sample to determine the spent hydrogen sulfide scavenger in the sample and/or determine scavenger uptake. The method may also include the step of adjusting the amount of scavenger introduced into the aqueous fluid in the tower in response to the scavenger uptake, to optimize the scavenger treatment in the scrubber or contactor tower.

6 Claims, 7 Drawing Sheets

Figure 1: MESA – 7220 Sodium Sulfide in Water Calibration Curve
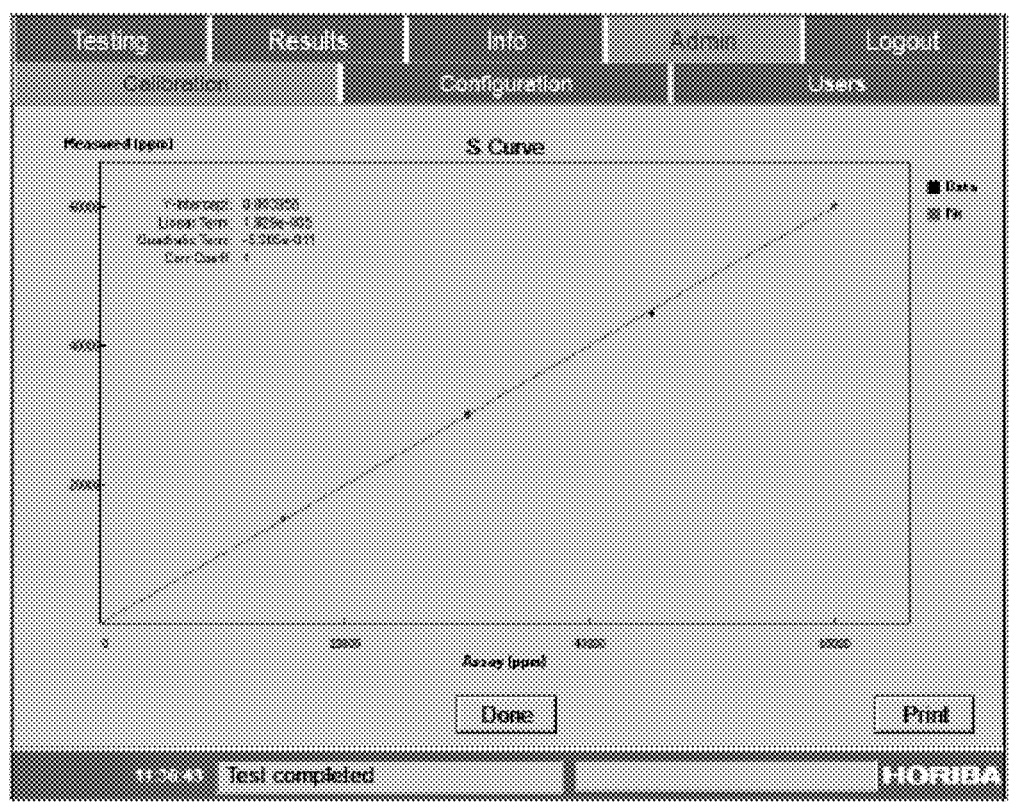

Figure 2: SLFA – 6800 Sodium Sulfide in Water Calibration Curve
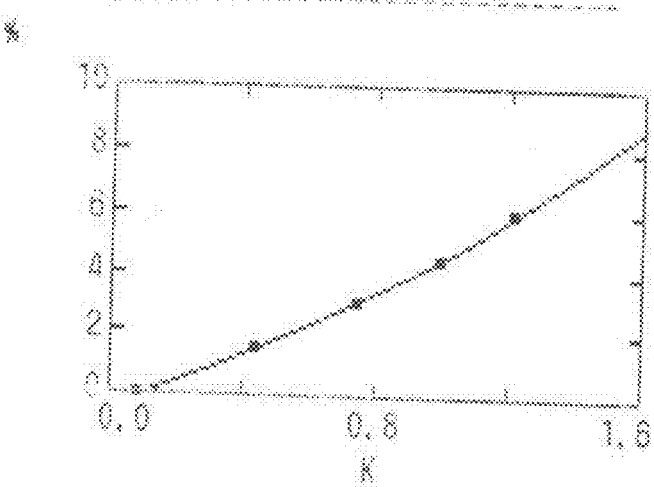

Figure 3: Calibration curve of 600 SX for the SLFA 6800 at low, medium, and high sulfur content range
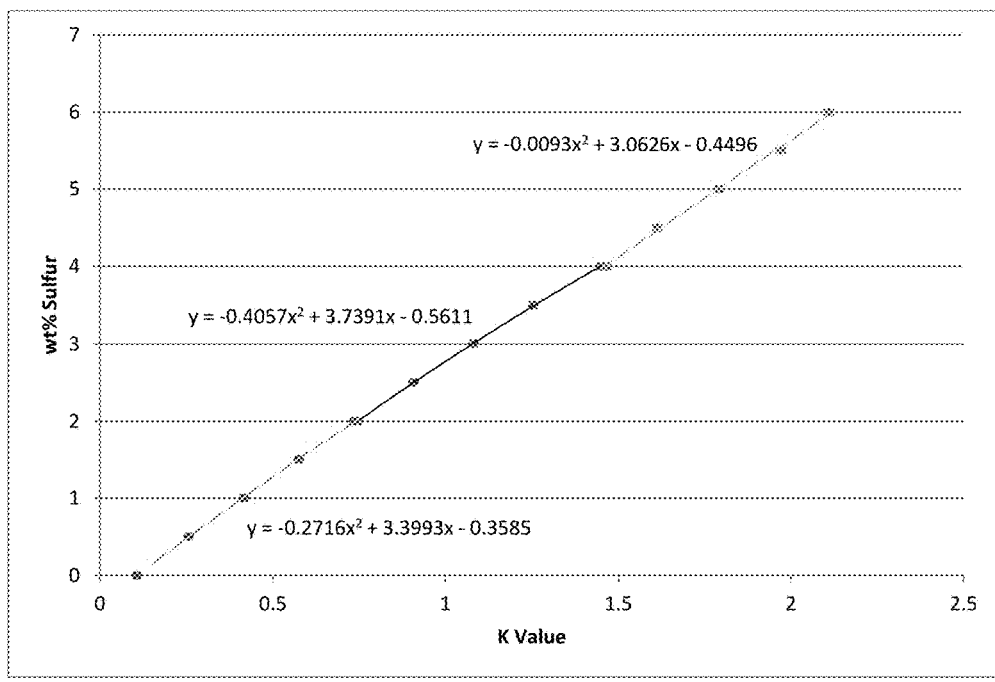

Figure 4: Field trial data with sulfur content of spent 600 SX triazine samples measured by both x-ray fluorescence and combustion analysis
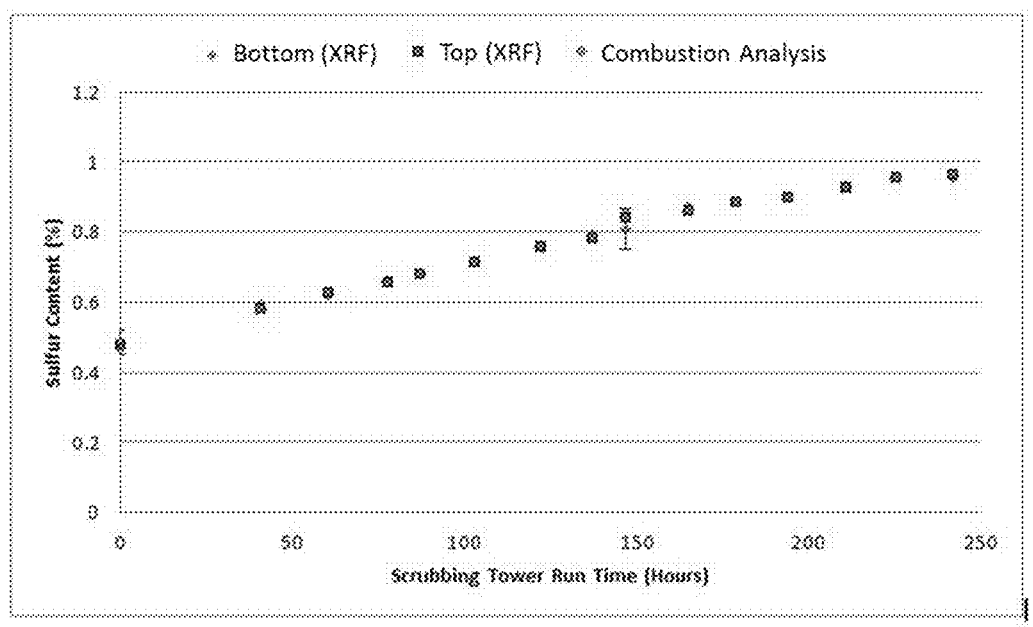

Figure 5: Calibration curve of 20 wt % monoethanolamine for the SLFA 6800
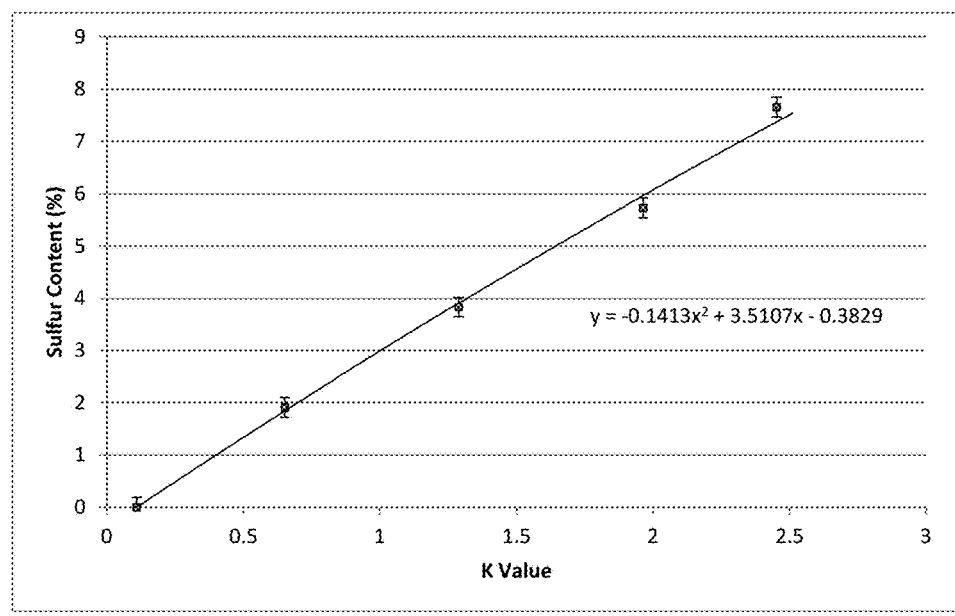

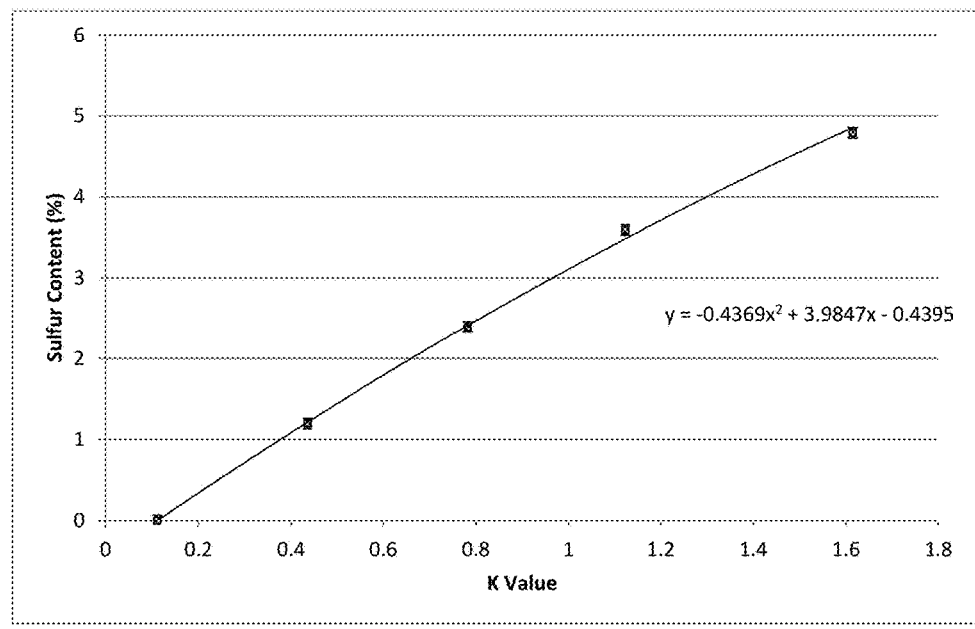
Figure 6: Calibration curve of 20 wt % diethanolamine for the SLFA 6800
$y = -0.4369x^2 + 3.9847x - 0.4395$ Figure 7: Calibration curve of 20 wt % triethanolamine for the SLFA 6800
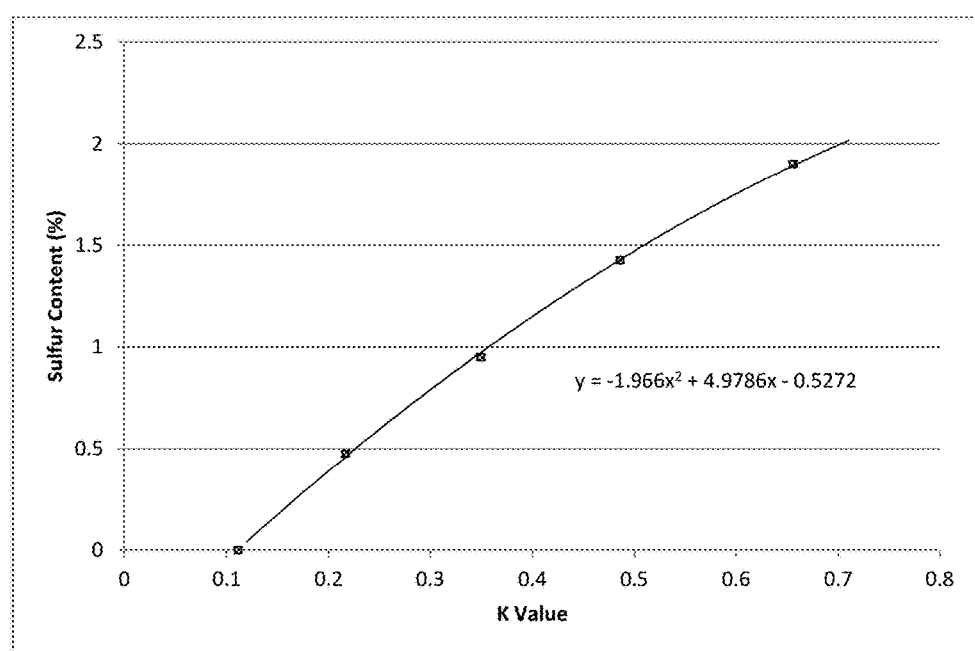

ANALYTICAL METHOD FOR OPTIMIZING EFFICIENCY OF HYDROGEN SULFIDE SCAVENGERS

CROSS REFERENCE TO RELATED APPLICATIONS

This application claims the benefit of priority of U.S. Provisional Patent Application No. 62/309,115 filed Mar. 16, 2016, the entire contents of which are hereby incorporated by reference in its entirety.

FIELD

The present disclosure relates generally to an apparatus and method of detecting and optimizing the efficiency of hydrogen sulfide scavengers. More particularly, the present disclosure relates to an apparatus and method for measuring the sulfur content in aqueous based fluids containing hydrogen sulfide scavengers which are used to remove hydrogen sulfide from hydrocarbons.

BACKGROUND

The hydrogen sulfide content of fluids from oil and gas wells has an important impact on the economic value of the produced hydrocarbons and production operations. Hydrogen sulfide is dangerous to personnel as it is extremely toxic to humans and is extremely corrosive to most metals. It can cause corrosion problems to drill strings, transport pipes, storage tanks, and other metal components. It causes sulfide stress cracking, hydrogen embrittlement and pitting corrosion in oil and gas operations. The removal of hydrogen sulfide from oil and gas streams is often required in order to meet many pipeline and storage regulations.

A number of processes are available to remove hydrogen sulfide from hydrocarbon streams using chemical agents. These chemical agents react with one or more sulfide species and convert them to a more inert form. These chemical agents are known in the industry as sulfur scavengers. Sulfur scavengers can be in a solid or liquid form. Liquid scavengers may be regenerative scavengers such as amine wash or reduction oxidation or non-regeneration scavengers such as aldehydes, triazines, and sodium nitrates, as examples. When the hydrogen sulfide concentration is low, non-regenerative liquid scavengers are often used.

A large number of non-regenerative chemical formulations exist for removal of hydrogen sulfide. One important group and the most frequently used liquid hydrogen sulfide scavengers are hexahydrotriazine-based hydrogen sulfide scavengers. These are commonly referred to in the industry as triazine scavengers. Triazines are readily deployed in scrubbers and are effective scavengers. Triazine is a heterocyclic structure similar to cyclohexane but with three carbons replaced by nitrogen atoms. The most common triazines used as hydrogen sulfide scavengers are monoethanolamine (MEA triazine) or methyl amine (MA triazine). Variations involving substitutions of the hydrogen atoms with other functional groups are used and different substitutions result in different reactivity with hydrogen sulfide, changes in the solubility of the triazine, and changes in the solubility of the reactant products. Triazine can therefore be tailored to better suit the application.

In one example, a liquid hydrogen sulfide scavenger, such as triazine, is used in a contactor tower or scrubber. The hydrocarbon feed gas is bubbled through the tower filled with an aqueous fluid containing triazine. As the hydrocarbon gas bubbles up through the aqueous based fluid, the hydrogen sulfide reacts with the triazine and the hydrogen sulfide is removed from the hydrocarbon gas stream.

The main byproduct of reacted triazine is dithiazine. Dithiazine is the result of two moles of hydrogen sulfide reacting with one mole of triazine. Dithiazine is easy to handle and dispose of. If the reaction proceeds further, a solid polymeric material believed to be a thioformaldehdye polymer substitution on the dithiazine molecule is formed. This solid material is hard to handle and dispose of, and can cause operational difficulties in scrubbing towers. Hence it is desirable from a cost perspective to maximize the formation of dithiazine while monitoring the progress of the reaction in order to minimize solids formation.

As a result, it is useful to be able to determine the amount of and efficiency of hydrogen sulfide scavenger in a system to be able to determine whether more or less scavenger should be added to the system. It would be useful to have a portable apparatus and a rapid testing method for determining the amounts of hydrogen sulfide scavenger and its byproducts in the liquid in the scrubber or contact tower.

Currently, there are limited options for rapid, portable techniques for measuring how much capacity is remaining in the scavenger as it is flowed through a scrubber or contactor tower. To measure sulfur in spent scavenger, a common method is combustion analysis. This method requires special equipment which is often difficult to set up in remote locations and if the equipment is not available on site, the transportation of samples can significantly delay analysis. As a result, it can be difficult to use this process for real time adjustments to a scavenging system. Other methods may be available on site but would require hours to conduct an analysis of samples or the results are not accurate.

While several products are available for detecting the level of hydrogen sulfide in crude oil, there are limited options for the effective and rapid determination of hydrogen sulfide scavengers in aqueous-based fluids.

It is, therefore, desirable to provide a portable apparatus and method for the rapid determination of hydrogen sulfide scavenger in an aqueous based sample.

SUMMARY

It is an object of the present disclosure to obviate or mitigate at least one disadvantage of previous systems and methods.

In a first aspect, the present disclosure provides a method of determining sulfur content in an aqueous fluid containing spent hydrogen sulfide scavenger, where the aqueous fluid includes a liquid hydrogen sulfide scavenger used to remove hydrogen sulfide from a gas stream, the method comprising: providing a sample of the aqueous fluid with the spent hydrogen sulfide scavenger; using x-ray fluorescence to determine the amount of total sulfur in the sample: and using the total sulfur content of the sample to determine the spent hydrogen sulfide scavenger in the sample.

In a further aspect, there is provided a use of x-ray fluorescence to determine sulfur content in an aqueous based solution including spent hydrogen sulfide scavenger, where the aqueous fluid comprises water and a liquid hydrogen sulfide scavenger used to remove hydrogen sulfide from a gas stream in a tower.

In a further aspect, the present disclosure provides a method of adjusting hydrogen sulfide scavenger treatment rates in a hydrogen sulfide scrubbing tower, the method comprising: providing a sample of an aqueous fluid from the scrubber tower, wherein the aqueous fluid includes spent hydrogen sulfide scavenger; using x-ray fluorescence to determine the amount of sulfur in the sample: and using the total sulfur content of the sample to adjust the hydrogen sulfide scavenger introduced into the aqueous fluid in the tower to optimize the hydrogen sulfide scavenger treatment rate in the tower.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

FIG. 1 is a graph showing results of XRF measurements for the MESA 7200.

FIG. 2 is a graph showing results of XRF measurements for the SLFA 6800.

FIG. 3 is a calibration curve of 600 SX for the SLFA 6800 at low, medium and high sulfur content range.

FIG. 4 is field trial data with sulfur content of spent 600 SX triazine samples measured by both x-ray fluorescence and combustion analysis.

FIG. 5 is a calibration curve of 20 wt % monoethanolamine for the SLFA 6800.

FIG. 6 is a calibration curve of 20 wt % diethanolamine for the SLFA 6800.

FIG. 7 is a calibration curve of 20 wt % triethanolamine for the SLFA 6800.

DETAILED DESCRIPTION

Generally, the present disclosure provides an analysis method for measuring sulfur content in an aqueous based fluid containing hydrogen sulfide scavenger. The fluid is used in contactor or scrubber towers for removing hydrogen sulfide from hydrocarbon gas streams passed through the tower. The method also allows for substantially real time adjustments to the concentration of the hydrogen sulfide scavenger in the tower to provide for a more efficient and economic scavenging system.

In the present disclosure, there is described a method for using X-ray fluorescence (XRF) methods to measure the remaining capacity and/or presence of spent scavenger in aqueous solutions. In one aspect of the invention, the method is used to measure the sulfur content in an aqueous fluid containing hydrogen sulfide scavenger from contactor towers or scrubbers. In another aspect, the method includes adjusting the amount of hydrogen sulfide scavenger added to the aqueous fluid in the tower.

XRF provides an elemental and chemical analysis of a material. In general terms, it bombards the material with high-energy x-rays or gamma rays which cause the emission of secondary or fluorescent x-rays from the material. When materials are exposed to short wavelength x-rays or gamma rays, ionization of their atoms may take place. This energy causes tightly held electrons from inner orbitals of the atom to be expelled. The removal of the electrons in this way makes the structure of the atom unstable and electrons in higher orbitals replace the missing electron in the lower orbital to fill the hole left behind. When this happens, energy is released in the form of a photon. The material emits radiation which has energy characteristic of the transition between specific electron orbitals in a particular element. Fluorescence indicates that the absorption of radiation of a specific energy results in the re-emission of radiation of a different energy. The fluorescent radiation can be analyzed by sorting the energies of the photons or by separating the wavelengths of the radiation. Once sorted, the intensity of each characteristic radiation is directly related to the amount of each element in the material. Conventional x-ray generators can be used and the output can be modified for the application, by changing power or wavelength.

As described above, concentrations of hydrogen sulfide in gas streams can be removed by flowing the gas stream through an aqueous fluid containing a liquid hydrogen sulfide scavenger. This is done in towers such as scrubbers, contactor towers, or sparging towers. The term "contactor towers" used herein refers to any such towers where gas streams are flowed through aqueous fluids containing liquid hydrogen sulfide scavengers to remove the hydrogen sulfide from the gas stream.

XRF methods have been used in the past to determine total sulfur in petroleum and petroleum products such as crude oil. However, these methods were found to be effective for higher concentrations of sulfur. Lower concentrations of sulfur result in higher errors and less effective measurements. Triazines and other non-regenerative hydrogen sulfide scavengers are often used in feed streams with lower concentrations of hydrogen sulfide, and often in systems having less than 1% (10,000 ppm) hydrogen sulfide. It was previously thought that XRF methods would not be effective with these lower concentrations of sulfur. It was also previously thought that XRF methods were not effective in oxygenate environments such as aqueous-based samples.

Other factors cause ineffective readings with XRF methods. Spectral interferences are caused by the closeness of the x-ray characteristic lines of the elements present in a sample and the limited ability to completely resolve them. Matrix effects are caused by concentration variations of the elements in a sample. These variations directly influence x-ray absorption and change the measured intensity of each element. For example, oxygenates may affect the apparent sulfur reading. Other matrix related interferences may arise from heavy metal additives, lead alkyls, and elements such as silicon, phosphorus, calcium, potassium, and the halides, especially if present at concentrations greater than one tenth of the measured concentration of sulfur. These types of interferences are always present in x-ray fluorescence analysis and are completely unrelated to spectral interferences.

As a result, the XRF methods must compensate using spectra deconvolution or overlap correction and inter-element correction by multiple regression or other mathematical methods.

In the present method, XRF methods are used to measure the sulfur content in aqueous based samples containing spent hydrogen sulfide scavenger. It was previously thought that the oxygen content of a sample of an aqueous solution with hydrogen sulfide scavenger would prevent the effective measurement of sulfur or spent scavenger. However, it has now been determined that XRF methods are effective and rapid methods for this measurement. This allows the measurement to be done substantially in real time and the scavenging system to be immediately moderated in response.

For use of the XRF method to detect sulfur in the scavenger stream, in one aspect, the feedstream has a hydrogen sulfide concentration of less than 5% and in another aspect, less than 2%. In a further aspect, the sulfur content of the scavenger containing stream is less than 1% sulfur, in another aspect, is less than 0.1% sulfur, and in further aspect, is about 10-1000 ppm sulfur.

The XRF instruments are calibrated using the matrix in which the sulfur will be present. This matrix is determined based on the make-up of the aqueous sample including the aqueous base, scavenger, other chemicals and any contaminants that may be present. The calibrations are done in accordance with the manufacturer's standard instructions for the specific XRF instrumentation. The calibration corrects for the oxygen interference but surprising still allows for an effective reading of the sulfur content, even at low sulfur concentrations.

Although the present method is described herein using triazine as the exemplified hydrogen sulfide scavenger, the XRF method is useful in systems using other hydrogen sulfide scavengers such as those set out above, including other non-regenerative hydrogen sulfide scavengers and regenerative hydrogen sulfide scavengers, for example amine systems.

The XRF testing of the aqueous samples may identify the sulfur load in the aqueous sample taken from the aqueous stream containing the hydrogen sulfide scavenger. This testing provides an accurate analysis of the sulfur in the scavenger stream. By measuring the sulfur content of the aqueous sample, the analysis would identify the amount of elemental sulfur removed from the hydrocarbon feedstream. Accordingly, the amount of hydrogen sulfide scavenger that was added to the tower could be adjusted accordingly.

The XRF method set out herein is carried out using instrumentation having an excitation energy at 4.5 KEV and fluorescence is measured at 2.32 KEV. This is in accordance with commercially available instrumentation. However, a wide range of excitation and fluorescence energies may be used, depending on the specific samples being tested and their content.

EXAMPLES

Examples 1 and 2

Testing was done on samples taken from a sparging tower using Horiba x-ray fluorescence sulfur analyzers, MESA 7200 multi-element analyser and SLFA xray fluorescence analyzer.

The SLFA applies energy dispersive x-ray fluorescence using an end window x-ray tube of 4.5 KEV to excite sulfur atoms in water products and cause x-ray fluorescence at 2.32 KEV. The instrument has a sample tray section, analyzer, with a detector, x-ray tube, data processor, microcomputer that stores up to fifteen calibration curves, a LED display, thermal printer, and 2 x-ray warning lights.

In operation, the measurement of total sulfur concentration is expected to be from 0-10 wt % in aqueous based samples, with a detection limit of 20 ppm. Repeatability of measurement can be 0.0015 wt % with standard deviation at n=10, with sample containing 1 wt % sulfur. C/H ratio error is ±0.0005 wt % sulfur with the sample containing 1 wt % sulfur.

Calibration of the instrument is done by optional standard solutions with 5-20 points of calibration. No helium purge is required to obtain low level ppm accuracy. Temperature range is +5 C to 40 C.

The testing procedure was as follows:
1. Calibration—
   Calibrate MESA—7220 with sodium sulfide in water. Measure the calibration standards at 180 seconds and 3 repeats.
   ii. Calibrate the SLFA—6800 with standard containing known amounts of sulfur content in the appropriate matrix in water. Measure the calibration standards at 100 seconds and 3 repeats.
2. Sample Preparation
   i. Transfer enough sample to fill the 2-piece cups.
   ii. Finish preparing the 2 piece cups.
3. Sample Measurements
   i. Measure the calibration standards against the new calibration curve at 180 seconds and 3 repeats for the SLFA—6800.
   ii. Measure the calibration standards against the new calibration curve at 100 seconds and 3 repeats for the SLFA—6800.

Results of the XRF measurements are shown in Table 1 below and FIG. 1 for the MESA 7200.

TABLE 1

| Test # | 0 ppm | 15000 ppm | 30000 ppm | 45000 ppm | 60000 ppm |
|---|---|---|---|---|---|
| Test 1 | 0.0 | 15274.8 | 30520.7 | 44926.5 | 59765.2 |
| Test 2 | 0.0 | 15206.1 | 30396.3 | 44795.4 | 59611.6 |
| Test 3 | 0.0 | 15197.0 | 30323.3 | 44838.3 | 59732.1 |
| Average | 0.0 | 15226.0 | 30413.4 | 44853.4 | 59703.0 |
| Std. Dev. | 0.0 | 42.5 | 99.8 | 66.8 | 80.8 |

Results of the XRF measurements are shown in Table 2 and FIG. 2 for the SLFA—6800.

TABLE 2

| Test # | 0 wt % | 1.5 wt % | 3 wt % | 4.5 wt % | 6 wt % |
|---|---|---|---|---|---|
| Test 1 | 0.00100 | 1.48122 | 3.04489 | 4.50568 | 5.89660 |
| Test 2 | 0.00074 | 1.47710 | 3.04351 | 4.49521 | 5.88314 |
| Test 3 | 0.00040 | 1.47808 | 3.04353 | 4.49167 | 5.85331 |
| Average | 0.00071 | 1.47880 | 3.04398 | 4.49752 | 5.87768 |
| Std. Dev. | 0.00030 | 0.00215 | 0.00079 | 0.00729 | 0.02215 |

These results show that the described XRF method of measuring the sulfur content of the water-based samples containing spent scavenger are effective for determining sulfur content. This measurement can then be used to determine any adjustments that may be necessary in the addition of hydrogen sulfide scavenger to the tower system.

Examples 3-7

Example 3

A sample of 600 SX was reacted with hydrogen sulfide forming the spent scavenger. The sulfur content of the spent scavenger was measured by combustion analysis. The sample was then diluted with fresh unreacted 600 SX to generate the calibration standards. Five standards were measured on the Horiba SLFA 6800 x-ray fluorescence spectrometer to generate each calibration curve. The calibration curve is shown in FIG. 3.

Example 4

Field samples of spent 600 SX were obtained from an operational bubble tower. For each sampling point two samples were drawn, one from the top of the tower and one from the bottom of the tower. The sulfur content was measured for all samples on the Horiba SLFA 6800 using the calibration curve in example 3. Results are shown in FIG. 4. Good agreement between the top and bottom tower samples was observed. In addition, the sulfur content for some samples was also measured by combustion analysis. Good correlation between the sulfur values measured by x-ray fluorescence and combustion analysis was attained.

Example 5

A sample of 20 weight percent monoethanolamine in water was saturated with hydrogen sulfide gas through a laboratory scale bubble tower. The sample was then diluted with fresh 20 weight percent monoethanolamine solution to generate the calibration standards. The sulfur content of the saturated monoethanolamine solutions were measured by combustion analysis. Five standards were then measured on the Horiba SLFA 6800 x-ray fluorescence spectrometer to generate each calibration curve. Results are shown in FIG. 5. Separate samples of 20 weight percent monoethanolamine in water containing an unknown amount of hydrogen sulfide were created with the sulfur content measured by both combustion analysis and x-ray fluorescence spectrometer. Good correlation was observed between the combustion analysis and SLFA 6800 calibration plot.

Example 6

A sample of 20 weight percent diethanolamine in water was saturated with hydrogen sulfide gas through a laboratory scale bubble tower. The sample was then diluted with fresh 20 weight percent diethanolamine solution to generate the calibration standards. The sulfur content of the saturated diethanolamine solutions were measured by combustion analysis. Five standards were then measured on the Horiba SLFA 6800 x-ray fluorescence spectrometer to generate each calibration curve. Results are shown in FIG. 6. Separate samples of 20 weight percent diethanolamine in water containing an unknown amount of hydrogen sulfide were created with the sulfur content measured by both combustion analysis and x-ray fluorescence spectrometer. Good correlation was observed between the combustion analysis and SLFA 6800 calibration plot.

Example 7

A sample of 20 weight percent triethanolamine in water was saturated with hydrogen sulfide gas through a laboratory scale bubble tower. The sample was then diluted with fresh 20 weight percent triethanolamine solution to generate the calibration standards. The sulfur content of the saturated triethanolamine solutions were measured by combustion analysis. Five standards were then measured on the Horiba SLFA 6800 x-ray fluorescence spectrometer to generate each calibration curve. Results are shown in FIG. 7. Separate samples of 20 weight percent triethanolamine in water containing an unknown amount of hydrogen sulfide were created with the sulfur content measured by both combustion analysis and x-ray fluorescence spectrometer. Good correlation was observed between the combustion analysis and SLFA 6800 calibration plot.

These results also show that the described XRF method of measuring the sulfur content of the water-based samples containing spent scavenger are effective for determining sulfur content.

In the preceding description, for purposes of explanation, numerous details are set forth in order to provide a thorough understanding of the embodiments. However, it will be apparent to one skilled in the art that these specific details are not required.

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

The invention claimed is:

1. A method of adjusting hydrogen sulfide scavenger treatment rates in a hydrogen sulfide scrubbing tower, the method comprising:
   a. providing a sample of an aqueous fluid from the scrubber tower, wherein the aqueous fluid includes spent hydrogen sulfide scavenger;
   b. using x-ray fluorescence to determine the amount of sulfur in the sample: and
   c. using the total sulfur content of the sample to adjust the hydrogen sulfide scavenger introduced into the aqueous fluid in the tower to optimize the hydrogen sulfide scavenger treatment rate in the tower.

2. The method of claim 1 wherein the hydrogen sulfide scavenger is triazine.

3. The method of claim 1 wherein the sulfur content of the aqueous based fluid is less than 1%.

4. The method of claim 3 wherein the sulfur content of the aqueous based fluid is less than 0.1%.

5. The method of claim 1 wherein the sulfur content of a gas stream in the scrubbing tower is less than 5%.

6. The method of claim 5 wherein the sulfur content of the gas stream is less than 2%.

* * * * *